(12) United States Patent
Bhullar et al.

(10) Patent No.: US 6,676,815 B1
(45) Date of Patent: Jan. 13, 2004

(54) CELL FOR ELECTROCHEMICAL ANALYSIS OF A SAMPLE

(75) Inventors: Raghbir Singh Bhullar, Indianapolis, IN (US); Brian Hill, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/476,442

(22) Filed: Dec. 30, 1999

(51) Int. Cl.[7] ............................................. G01N 27/327
(52) U.S. Cl. ........................... 204/403.03; 204/403.01; 204/403.14; 204/409
(58) Field of Search .................... 204/403, 409, 204/400, 416, 403.01, 403.03, 403.12, 403.14; 422/82.01, 82.02, 82.03

(56) References Cited

U.S. PATENT DOCUMENTS

| | | | |
|---|---|---|---|
| 4,514,276 A | | 4/1985 | Covington et al. |
| 4,966,671 A | | 10/1990 | Nylander et al. |
| 4,985,130 A | * | 1/1991 | Hale ........................... 204/415 |
| 5,130,009 A | * | 7/1992 | Marsoner et al. ...... 204/403.11 |
| 5,223,114 A | * | 6/1993 | Zare et al. ................... 204/601 |
| 5,741,639 A | * | 4/1998 | Ensing et al. ................... 435/6 |
| 5,762,770 A | * | 6/1998 | Pritchard et al. ...... 204/403.14 |
| 6,134,461 A | * | 10/2000 | Say et al. ................... 600/309 |
| 6,143,164 A | * | 11/2000 | Heller et al. ........... 204/403.11 |

FOREIGN PATENT DOCUMENTS

| | | |
|---|---|---|
| EP | 780 692 A2 | 6/1997 |
| EP | 827 177 A2 | 3/1998 |
| WO | WO 97/18464 | 11/1996 |

OTHER PUBLICATIONS

Niwa et al, Anal. Chem., pp. 68, 1865–1870, 1996.*

* cited by examiner

*Primary Examiner*—Kaj K. Olsen
(74) *Attorney, Agent, or Firm*—Brinks Hofer Gilson & Lione

(57) ABSTRACT

According to an aspect of the invention, a cell for electrochemical analysis is provided, comprising a body having a chamber, and a pair of electrodes opposing each other within the camber comprising a electrically conductive rod extending through the body transverse to the longitudinal direction and removed within the capillary channel. According to a preferred embodiment, at least one reagent is provided within the capillary channel. The cell may be part of a plurality of such cells connected in seriatim.

13 Claims, 4 Drawing Sheets

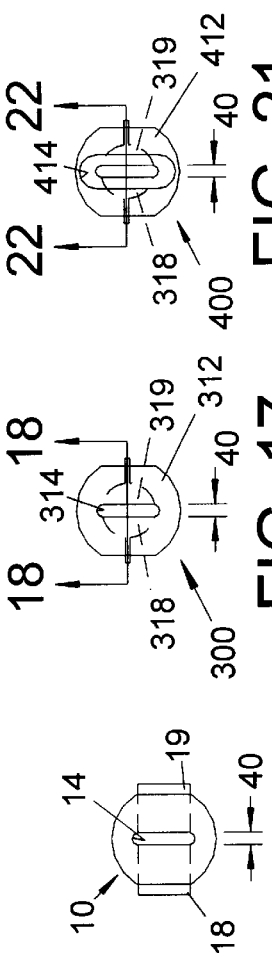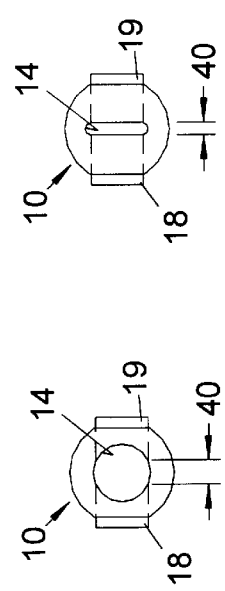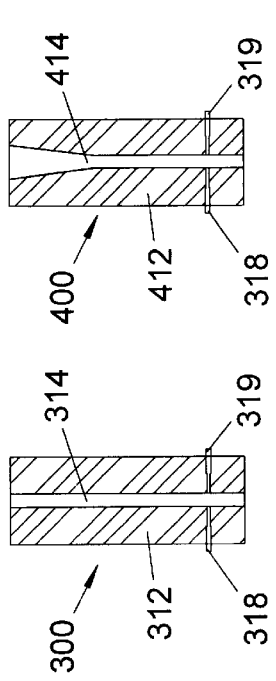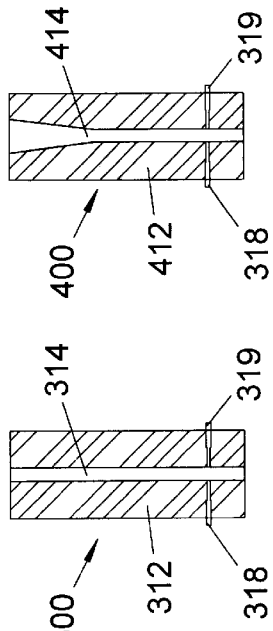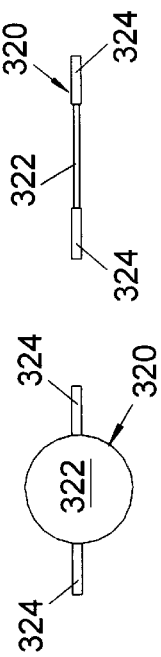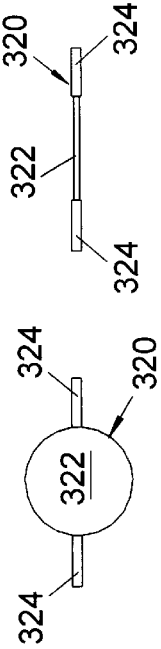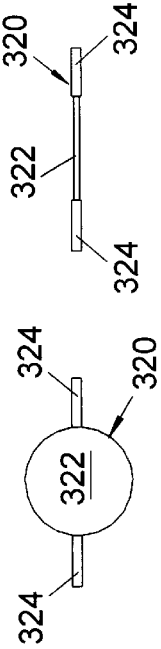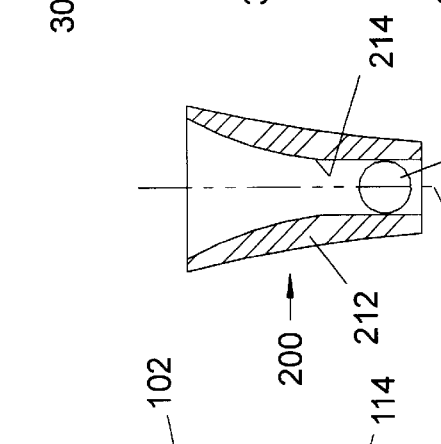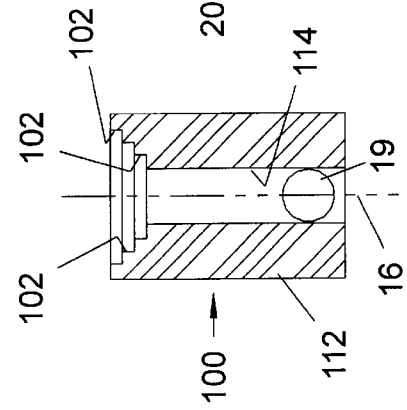

CELL FOR ELECTROCHEMICAL ANALYSIS OF A SAMPLE

BACKGROUND OF THE INVENTION

The present invention relates to test cells for electrochemical analysis.

Test cells for electrochemical analysis are well known. They have been used to determine the concentration of various analytes from biological samples, particularly from blood. Cells for electrochemical analysis are described in U.S. Pat. Nos. 5,413,690; 5,762,770 and 5,798,031; as well as in International Publication No. WO99/13101, each of which are hereby incorporated by reference.

An electrochemical biosensor typically includes a sensor strip. The sensor strip includes a space that holds the sample to be analyzed, may include reagents to be released into the sample, and includes an electrode set. The electrode set normally includes an insulating substrate, and electrodes that contact the sample, which have contact pads for electrically connecting the electrodes to the electronics of an analysis apparatus.

SUMMARY OF THE INVENTION

According to an aspect of the invention, a cell for electrochemical analysis is provided, comprising a body having a chamber, and a pair of electrodes opposing each other within the chamber comprising a metal rod extending through the body transverse to the longitudinal direction and removed within the capillary channel. According to a preferred embodiment, at least one reagent is provided within the capillary channel. The cell may be part of a plurality of such cells connected in seriatim.

According to a further aspect of the invention, a method of making a cell for electrochemical analysis is provided, comprising molding a body with a metal rod, forming a capillary channel transverse to the metal rod, and removing the metal rod from within the capillary channel thereby forming a pair of opposing electrodes. According to a preferred embodiment, the method further comprises depositing at least one reagent within the capillary channel. According to a further aspect of the invention, the method comprises molding a body as a parallel row of cell bodies with a metal rod transverse to the row of cell bodies.

According to a further aspect of the invention, a method of electrochemically analyzing a sample is provided, comprising drawing the sample within a cell for electrochemical analysis of the type described above, and applying a difference in electrical potential across the electrodes.

Many fluid samples may be analyzed according to the numerous aspects of the invention. For example, human body fluids such as whole blood, blood serum, urine, and cerebrospinal fluid may be measured. Also fermentation products and in environmental substances, which potentially contain environmental contaminants, may be measured.

BRIEF DESCRIPTION OF THE DRAWINGS

FIG. 13 presents an end view of a cell according to an aspect of the invention.

FIG. 14 presents an end view of a cell having a chamber with an oblong cross-section, according to a further aspect of the invention.

FIG. 15 is a side cross-sectional view of a cell having a chamber that is enlarged at one end, according to a further aspect of the invention.

FIG. 16 is a side cross-sectional view of a cell having a chamber that is enlarged at one end, according to a further aspect of the invention.

FIG. 17 is an end view of a cell according to a further aspect of the invention.

FIG. 18 is a side cross-sectional view of the FIG. 17 cell taken along line 18—18 of FIG. 17.

FIG. 19 is an enlarged top pan view of a rod according to an aspect of the invention.

FIG. 20 is a side view of the FIG. 19 rod.

FIG. 21 is an end view of a cell according to a further aspect of the invention.

FIG. 22 is a side cross-sectional view of the FIG. 21 cell taken along line 22—22 of FIG. 21.

DETAILED DESCRIPTION

Figure 1:
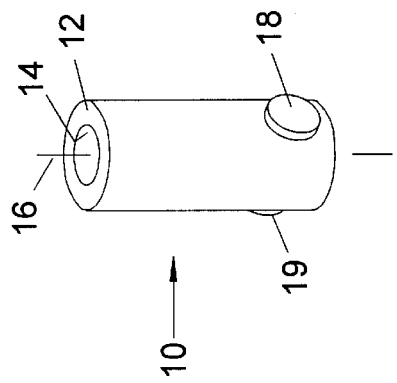
FIG. 1 presents a perspective view of an cell for electrochemical analysis according to an aspect of the invention.
Figure 2:
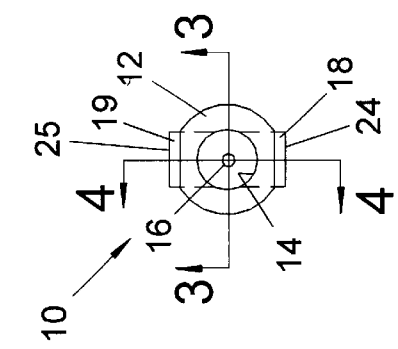
FIG. 2 presents a top plan view of the FIG. 1 cell.
Figure 3:
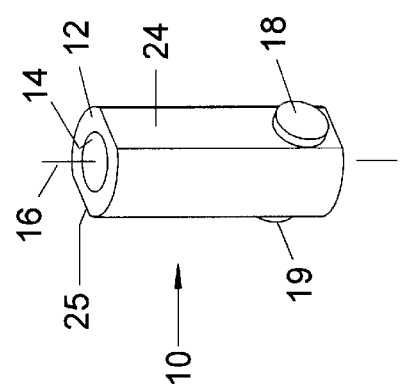
FIG. 3 presents a side cross-sectional view taken along line 3—3 of FIG. 2.
Figure 4:
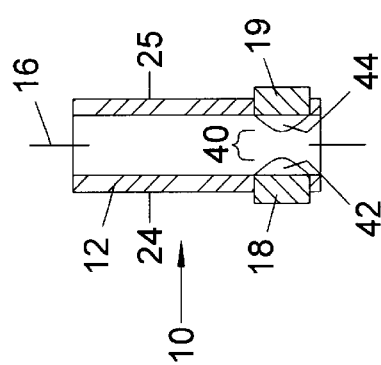
FIG. 4 presents a side cross-section view taken along line 4—4 of FIG. 2.

Various aspects of the invention are presented in FIGS. 1–22, which are not drawn to scale and wherein like components are numbered alike. Referring now to FIGS. 1–4, numerous views of a cell 10 for electrochemical analysis are presented according to an aspect of the invention. FIG. 1 presents a perspective view of the cell 10, FIG. 2 presents a top plan view, FIG. 3 presents a side cross-sectional view taken along line 3—3 of FIG. 2, and FIG. 4 presents a side cross-sectional view taken along line 4—4 of FIG. 2.

The cell 10 comprises a cell body 12 of dielectric material having a chamber 14 extending in a longitudinal direction 16. In the example presented in FIGS. 1–4, the cell body 12 is an annular wall that defines the chamber 14. A pair of electrodes 18 and 19 opposing each other within the chamber comprise a rod of electrically conductive material extending through the cell body 12 transverse to the longitudinal direction 16 and removed within the chamber 14. The chamber 14 divides the rod of electrically conductive material, thereby forming the pair of opposing electrodes 18 and 19. The rod of electrically conductive material preferably extends in a direction perpendicular to the longitudinal axis 16 of the cell body 12 (particularly if cylindrical) or the chamber 14. As used herein, the term "perpendicular" is intended to indicate an angle on the order of 90°, and is intended to include moderate deviations from exactly 90° to the extent that functionality of the electrochemical cell is not adversely effected. Some variation is inevitable in a manufacturing process.

The pair of electrodes 18 and 19 penetrate the annular wall of the cell body 12 within the chamber 14. The metal rod, and hence the electrodes 18 and 19, may be circular in cross section (as shown), or square, rectangular, triangular, polygonal, or any other shape suitable for an electrode. According to a preferred embodiment, the chamber 14 is a capillary channel and extends all the way through the cell body 12.

As best shown in FIG. 4, the size and location of the chamber 14 are such that the rod of electrically conductive material is divided with a dielectric gap 40 between a first portion 42 that terminates at the inner wall of the chamber 14 on one side of the chamber 14 and a second portion 44 that terminates at the inner wall of the chamber 14 on an opposite side of the chamber 14. The rod of electrically conductive material passes from one side to the other, but is divided. The gap 40 is presented from another view in FIG. 13 as seen looking into one of the ends of cell 10. Another view of the gap 40 is presented in FIG. 14 wherein the chamber 14 is oblong transverse to the axis of the rod. According to a preferred embodiment, the gap 40 is within the range, inclusive, of 1 micrometer to 3000 micrometers. According to a more preferred embodiment, the gap 40 is within the range, inclusive, of 5–1000 micrometers. According to a particularly preferred embodiment, the gap 40 is on the order 25 micrometers.

Referring again to FIGS. 1–4, the cell body 12 is preferably injection molded around the rod, thus embedding the rod in the cell body 12, and the rod is removed from within the chamber 14 by, for example, mechanical or laser drilling using machining methods known in the art thereby reducing the rod to individual electrodes 18 and 19. The diameter of the hole drilled is preferably slightly larger than the diameter of the rod so that the two electrodes are separated and electrically insulated from each other, as shown in FIG. 4. The hole drilled may be circular in cross-section. The chamber 14 may be partially molded, and the chamber 14 may be fully or partially formed by removing the dielectric material forming the body 12.

Examples of metals that may be implemented in forming the electrodes 18 and 19 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. Preferably, the electrode set is constructed of gold, platinum, palladium, iridium, or alloys of these metals, since such noble metals and their alloys are unreactive in biological systems. The rod may be a material or a metal other than a noble metal, for example graphite or copper. In such case, the surface of the electrodes 18 and 19 within the chamber may be plated with a noble metal after the metal rod is removed from within the chamber 14, for example by immersion or electroless plating.

The volume of chamber 14 within the electrochemical cell may be relatively small, such as 5 microliters or less. Volumes as small as 1 microliter or less are envisioned in the practice of the invention. Volume of the chamber 14 may be reduced by reducing the height of the cell 10 in the longitudinal direction 16, by reducing the diameter of the chamber 14, and/or by making the chamber oblong, as presented in FIG. 14.

Referring now to FIGS. 15 and 16, the chamber 14 need not have a constant cross-section section. For example, it may have a smaller diameter at one end of the body than the other. Referring now specifically to FIG. 15, a cell 100 having a body 112 and a chamber 114 is presented wherein the chamber 114 is enlarged on one end by a plurality of concentric circular sections 102, each section 102 closer to the end of the cell 100 having a larger diameter than the previous one. Referring now specifically to FIG. 16, a cell 200 having a body 212 and a chamber 214 is presented wherein the chamber 214 is enlarged on one end and reduces in diameter with curvilinear sloping sides to the reduced diameter on the other end. Enlarging the chamber on one end facilitates applying the sample to the cell particularly if done manually.

Figure 5:
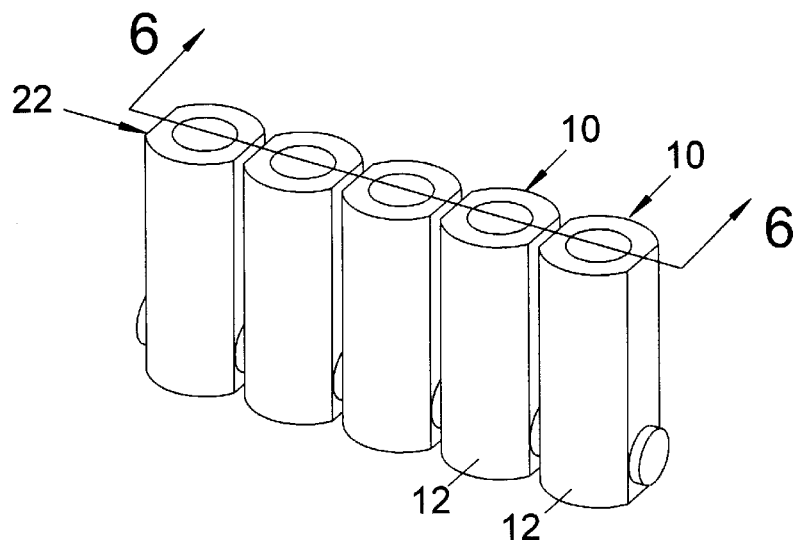
FIG. 5 presents a perspective view of a body comprising a plurality of cell bodies, according to a further aspect of the invention.
Figure 6:
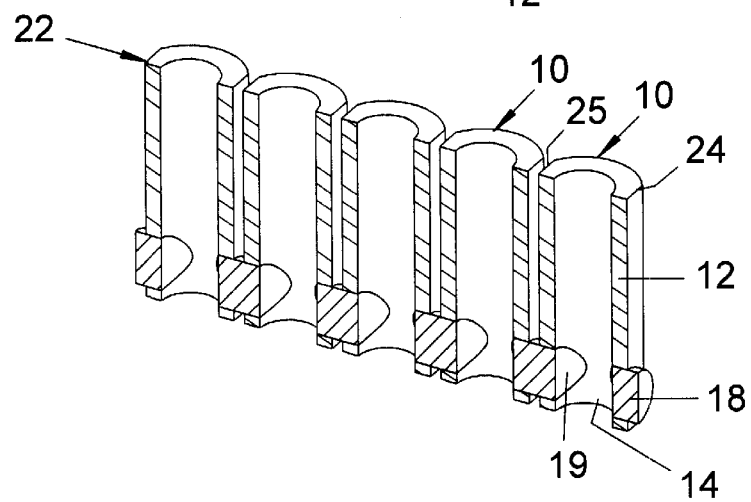
FIG. 6 presents a perspective cross-sectional view taken along line 6—6 of FIG. 5.
Figure 7:
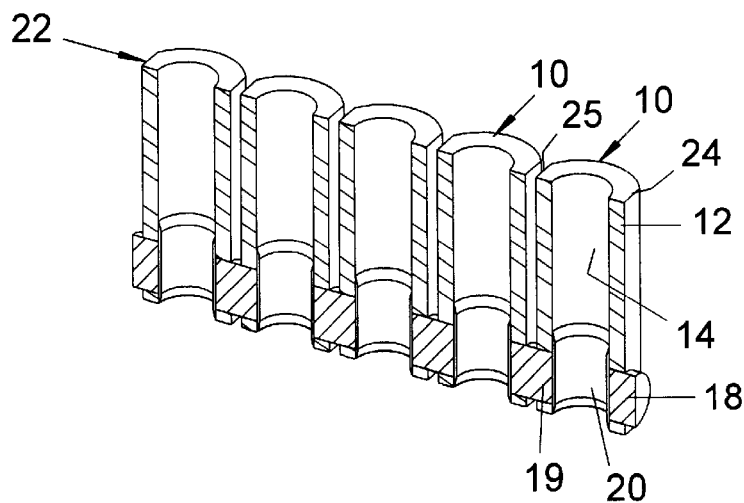
FIG. 7 presents the perspective cross-sectional view of FIG. 6 with a reagent deposited within the cells.

Referring now to FIG. 5, a perspective view of an embodiment is presented wherein the cell 10 is part of a plurality of cells 10 connected in seriatim. FIG. 6 presents a cross-sectional view of the cells 10 of FIG. 5 taken along line 6—6 of FIG. 5. Each chamber 14 divides the rod of electrically conductive material. FIG. 7 presents a view identical to FIG. 6, except the cells 10 further comprise at least one reagent 20 within the chamber 14. In the example presented, the at least one reagent 20 is deposited on the cell body 12 within the chamber 14 and overlying the electrodes 18 and 19. The cells 10 connected in seriatim as shown in FIGS. 5–7 may be used in that form, or may be separated into individual cells 10, as shown in FIGS. 1–4.

The reagent may be deposited, for example, by dipping the cell into the reagent in liquid form to a depth that deposits the reagent at the desired level within the chamber 14. For a capillary chamber 14, the reagent may be drawn into the cell body 12 via capillary action. The reagent may reach an equilibrium level that may correspond to the desired level within the chamber 14. If the desired level is less than the equilibrium level, then the cell 10 is dipped for a period of time that is less than the time it takes for the reagent to reach the equilibrium level with the chamber 14. If the desired level is greater than the equilibrium level, then the cell 10 is dipped a greater distance into the reagent.

According to a further aspect of the invention, with reference to FIGS. 1–4, a method of making a cell 10 for electrochemical analysis is provided, comprising molding a cell body 12 with a metal rod, forming a chamber 14 transverse to the metal rod, removing the metal rod from within the chamber 14 thereby forming a pair of opposing electrodes 18 and 19. The method may further comprise depositing at least one reagent within the chamber 14, for example, by drawing the reagent into the chamber 14 in liquid form via chamber action. As presented in FIGS. 5–7, the method may further comprise forming a plurality of parallel chambers 14 in the cell body 12 and removing the metal rod from within each chamber 14. The chamber 14 may be at least partially formed while molding the cell body 12.

According to a further aspect of the invention, with reference to FIGS. 5–7, a method of making a cell 10 for electrochemical analysis is provided, comprising molding a body 22 as a parallel row of cell bodies 12 with a metal rod transverse to the row of cell bodies 12, forming a plurality of parallel chambers 14 in the body 22 transverse to the metal rod, one chamber 14 for each the cell body 12, and removing the metal rod from within each chamber 14. The method may further comprise separating the cell bodies 12, thereby forming individual cells 10.

Figure 8:
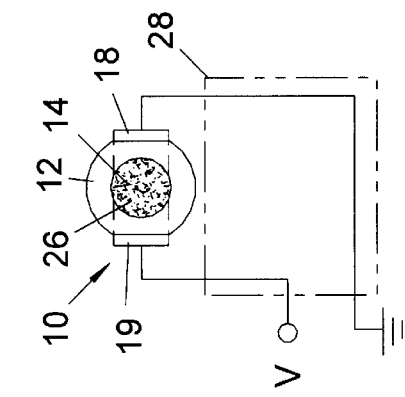
FIG. 8 presents a perspective of a cell for electrochemical analysis according to a further aspect of the invention.
Figure 9:
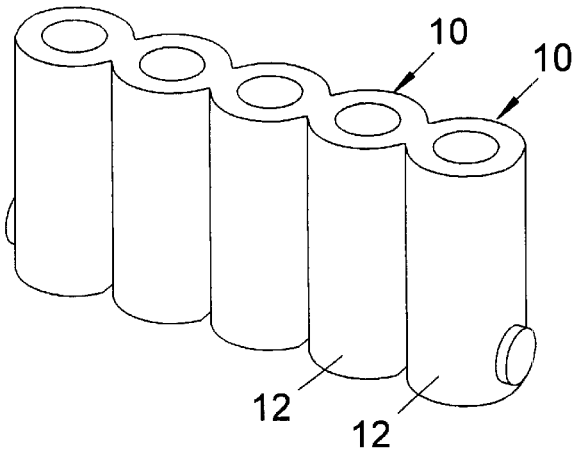
FIG. 9 presents a perspective view of a body comprising a plurality of cell bodies, according to a further aspect of the invention.

The cell body 12 of FIGS. 1–4 is cylindrical with a pair of opposing planar sides 24 and 25 aligned with the electrodes 18 and 19 and extending in the longitudinal direction 16, and the body 22 of FIGS. 5–7 is molded as a row of discrete cell bodies 12 interconnected by the metal rod that forms the electrodes 18 and 19. Referring now to FIG. 8 (first drawing sheet), a cell 10 is presented having cylindrical cell body 12 without the planar sides 24 and 25. The cross-sectional shape of cell body 12 may also be square, rectangular, polygonal, or any other shape suitable for use in a cell 10. Referring now to FIG. 9 (third drawing sheet), the body 22 may comprise a parallel row of cell bodies having a cylindrical cross-section. In the example presented, the body 22 is monolithic. It may be implemented in the monolithic form, or planar sides 24 and 25 (FIGS. 1–7) may be formed by machining the body 22, or the cell bodies 12 may be otherwise rendered discrete and interconnected by the metal rod.

Figure 10:
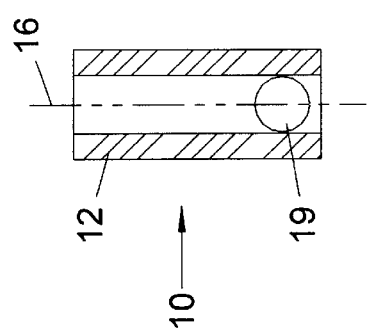
FIG. 10 presents a schematic view of a sample analysis method and apparatus.

Referring now to FIG. 10, a method of electrochemically analyzing a sample 26, comprising drawing the sample into a cell 10 for electrochemical analysis and applying a difference in electrical potential, indicated as V, across the electrodes 18 and 19. An electrochemical reaction commences, particularly where the electrodes 18 and 19 are closest together, that is indicative of a chemical property of the sample. The indication may be in the form of a current, an impedance, or other measurement, as is known in the art. The method may further comprise suspending at least one reagent in the sample, preferably by depositing the at least one reagent being deposited on the cell body 12 within the chamber 14 before drawing the sample 26 into the chamber.

Placing the electrodes 18 and 19 close together is advantageous as closer proximity tends to decrease the time it takes to make a measurement. The novel manufacturing method of the invention creates a pair of opposing fingers in the side wall of the cell 12 that are in very close proximity, as best shown in FIGS. 4 and 6. The center of the chamber and the center of the metal rod are preferably aligned, and the diameter of the hole drilled through the metal rod while forming the electrodes 18 and 19 is preferably slightly larger than the diameter of the rod so that the two electrodes are separated and electrically insulated from each other, but preferably not larger than needed to reliably and repeatedly separate the electrodes, taking manufacturing tolerances and other manufacturing process variations into account.

An analysis device 28 (shown in phantom) is typically provided to measure current, impedance, or other property. The analysis device may be provided with an electrical connector, and the electrochemical cell 10 is inserted into the electrical connector in contact with the electrodes 18 and 19, manually or by an automatic feeding mechanism. The electrochemical cell 10 may be used in individual form, as presented in FIGS. 1–4 and 8, and/or as an interconnected row as presented in FIGS. 5–7 and 9 with an appropriate electrical connector that contacts each set of electrodes 18 and 19. Examples of measuring apparatus that may be adapted for use with the cells of the present invention are disclosed in U.S. Pat. Nos. 4,963,814; 4,999,632; 4,999,582; and 5,243,516, and U.S. patent application Ser. No. 08/996,280, filed Dec. 22, 1997 to Beaty et al.

Figure 11:
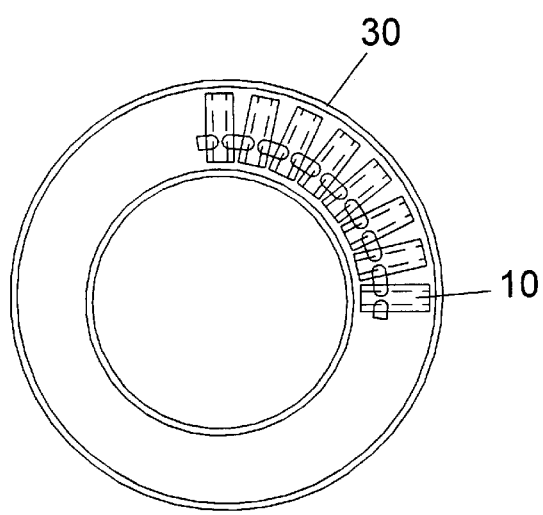
FIG. 11 presents a top plan view of a rotary clip for use with the cell of the invention.
Figure 12:
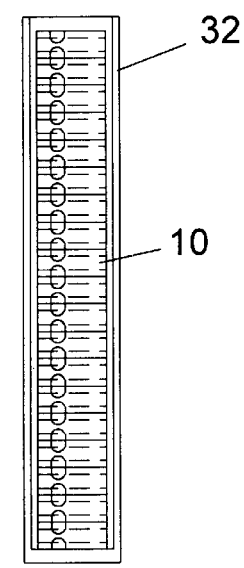
FIG. 12 presents a side plan view of a linear clip for use with the cell of the invention.

Referring now to FIGS. 11 and 12, a rotary clip 30 and a linear clip 32 are presented, according to a further aspect of the invention, for product packaging of the electrochemical cell 10. The cells 10 may be stacked horizontally, vertically, and/or helically within the clips 30 and 32. The bodies may also be oriented radially or circumferentially in the rotary clip 30. The rotary clip 30 may be configured as a carousel. The cells may or may not be connected in seriatim within the clips 30 and 32. The clips 30 and 32 are particularly desirable for use with an automatic analysis device 28.

Referring now to FIGS. 17 and 18, a cell 300 is presented according to a further aspect of the invention. FIG. 18 is a cross-sectional view taken along line 18—18 of FIG. 17. Cell 300 has a body 312, a chamber 314, and electrodes 318 and 319. The chamber 314 is oblong transverse to the axis of the rod that forms the electrodes 318 and 319, and the rod is removed from within the chamber 314, as previously described herein. Referring now to FIGS. 19 and 20, a top plan view and a side elevational view of a rod 320 is presented of the type used to form the electrodes 318 and 319. The rod 320 comprises a disk 322 with fingers 324 extending therefrom on opposite sides of the disk 322. The rod 320 may be formed, by example, by periodically stamping disks 322 in a rod of constant cross-section.

Referring now to FIGS. 21 and 22, a cell 400 is presented according to a further aspect of the invention. Cell 400 has a body 412, a chamber 414, and the electrodes 318 and 319. The chamber 414 is oblong transverse to the axis of the rod that forms the electrodes 318 and 319, and the rod is removed from within the chamber 414, as previously described herein. The chamber 414 is enlarged on one end thereby forming a funnel shape. The various features of the numerous embodiments presented herein may be used alone, or in combination with one or more other features, thus creating innumerable variations all according to aspects of the invention.

The reagent 20 provides electrochemical probes for specific analytes. The choice of specific reagent 20 depends on the specific analyte or analytes to be measured, and are well known to those of ordinary skill in the art. An example of a reagent that may be used in cell 10 of the present invention is a reagent for measuring glucose from a whole blood sample. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in WO 99/30152, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate butter), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference. A hematocrit reagent is preferably not deposited on the surface of the electrodes 18 and 19. It may be deposited within the chamber 14 at an end opposite to the electrodes 18 and 19.

Other non-limiting examples of enzymes and mediators that may be used in measuring particular analytes in sensor 20 of the present invention are listed below in Table 1. The electrochemical cell of the invention may have a plurality of reagents deposited on the cell body within the chamber.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is appreciated that a variety of electrochemical assays may be conducted with sensor 10 in accordance with this disclosure.

According to a preferred embodiment, the reagents are applied in liquid form and dried. As used herein, the term "dry" or "dried" is intended to mean removing water from the reagent to the point where it is immobile, chemically stable, and reactive when it comes in contact with the sample. The cell of the present invention may also include microspheres, as described in pending patent application entitled "MICROSPHERE CONTAINING SENSOR", U.S. patent application Ser. No. 09/471,571, inventors Raghbir Singh Bhullar and Brian S. Hill, filed Dec. 23, 1999, hereby incorporated by reference. The microspheres decrease sample size and improve flow of the sample within the cell. A reagent may be deposited on the microspheres.

Referring again to FIGS. 5–7, in one embodiment, the body 12 cells 10 are formed by injection molding polycarbonate around a solid gold rod on the order 500 micrometers in diameter. A suitable rod is available from ENGELHARD—CLAL LP, of New Jersey, U.S.A. The chamber 14 is mechanically drilled having a diameter on the order of 500 micrometers. The central axis of the drilling operation is aligned with the central axis of the rod, and perpendicular thereto. The actual diameter of the rod is typically slightly less than the nominal diameter of 500 micrometers. Conversely, the actual diameter of the chamber drilled is typically slightly larger than the nominal diameter of 500 micrometers. The result is that the rod is divided into to electrodes separated by dielectric gap 40 having a desirable width. The cell 10 according to this embodiment has a length in the longitudinal direction on the order of 36 millimeters and an outside diameter on the order of 16 millimeters. The flat faces 24 and 25 are on the order of 14 millimeters apart.

Products made by the methods disclosed herein are also represent further aspects of the invention. Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. An electrochemical cell assembly comprising:
 a plurality of cell bodies connected in seriatim, each cell body comprising a dielectric material and having an inner wall defining a longitudinal chamber;
 a pair of opposing electrically conductive electrodes embedded in each cell body, said electrodes in said plurality of connected bodies comprising segments of a common rod of electroconductive material; and
 a reagent deposited within the chamber, said reagent comprising at least one agent reactive with an analyte for electrochemically determining the concentration of the analyte in a biological sample.

2. The electrochemical cell assembly of claim 1, wherein at least one of said chambers comprises a capillary channel.

3. The electrochemical cell assembly of claim 2, wherein the reagent is dried in the capillary channel overlying the electrodes.

4. The electrochemical cell assembly of claim 2, wherein said capillary channel extends longitudinally all the way through said body.

5. The electrochemical cell assembly of claim 2, wherein the inner wall defining said capillary channel is not of constant cross-section.

6. The electrochemical cell assembly of claim 1, wherein said opposing electrodes are separated by a gap of between 5 and 1000 micrometers.

7. The electrochemical cell assembly of claim 6, wherein said gap is on the order of 25 micrometers.

8. The electrochemical cell assembly of claim 1, wherein said electrodes comprise a noble metal, copper or carbon, or a noble metal plated over copper or carbon.

9. The electrochemical cell assembly of claim 1, wherein said capillary channel has a volume not exceeding 1 microliter.

10. The electrochemical cell assembly of claim 1, wherein the inner wall defining at least one of said chambers is of constant cross-section.

11. The electrochemical cell assembly of claim 1, wherein said reagent comprises at least one enzyme.

12. The electrochemical cell assembly of claim 1, wherein said reagent comprises an enzyme and a mediator, said enzyme comprising glucose dehydrogenase and said mediator comprises ferricyanide.

13. The electrochemical cell assembly of claim 1, wherein said reagent comprises more than one enzyme and a mediator, said more than one enzyme comprising glucose dehydrogenase and diaphorase, and said mediator comprising ferricyanide.

* * * * *